(12) United States Patent
Weigel et al.

(10) Patent No.: US 11,510,837 B2
(45) Date of Patent: Nov. 29, 2022

(54) LEG PULLING DEVICE

(71) Applicant: CONDOR MEDTEC GMBH, Salzkotten (DE)

(72) Inventors: Lothar Weigel, Brakel (DE); Dominik Schulte, Salzkotten (DE); Christian Henke, Steinheim (DE)

(73) Assignee: CONDOR MedTech GmbH, Salzkottten (DE)

( * ) Notice: Subject to any disclaimer, the term of this patent is extended or adjusted under 35 U.S.C. 154(b) by 431 days.

(21) Appl. No.: 16/614,550

(22) PCT Filed: May 2, 2018

(86) PCT No.: PCT/DE2018/100417
§ 371 (c)(1),
(2) Date: Nov. 18, 2019

(87) PCT Pub. No.: WO2018/210375
PCT Pub. Date: Nov. 22, 2018

(65) Prior Publication Data
US 2020/0170870 A1    Jun. 4, 2020

(30) Foreign Application Priority Data

May 17, 2017 (DE) .................... 10 2017 208 306

(51) Int. Cl.
*A61F 5/048* (2006.01)
*A61G 13/12* (2006.01)
*A61G 13/00* (2006.01)

(52) U.S. Cl.
CPC ....... *A61G 13/125* (2013.01); *A61G 13/0081* (2016.11); *A61G 2203/32* (2013.01); *A61G 2203/34* (2013.01); *A61G 2210/50* (2013.01)

(58) Field of Classification Search
CPC ............. A61G 13/125; A61G 13/0081; A61G 2210/50; A61G 2203/32; A61G 2203/34; A61F 5/04; A61F 5/042; A61F 5/048; A61H 1/0244; A61H 1/0255
See application file for complete search history.

(56) References Cited

U.S. PATENT DOCUMENTS

| | | | |
|---|---|---|---|
| 9,561,148 B2 | 2/2017 | Friedrich | |
| 2010/0228157 A1 | 9/2010 | Tom | |
| 2010/0249672 A1 | 9/2010 | Ewing | |
| 2018/0303696 A1 | 10/2018 | Koenig et al. | |

FOREIGN PATENT DOCUMENTS

| | | |
|---|---|---|
| DE | 202012101347 U1 | 8/2012 |
| DE | 102011051937 A1 | 12/2012 |
| DE | 202012104964 U1 | 2/2014 |
| DE | 102015117596 B3 | 8/2016 |
| EP | 1364636 A1 | 11/2003 |

OTHER PUBLICATIONS

T&T Medilogic, DE 20 2012 109964 U1, English Translation (attached).*
Frolhoff, DE 20 2012 101347 U1, English Translation (attached).*

* cited by examiner

*Primary Examiner* — Camtu T Nguyen
(74) *Attorney, Agent, or Firm* — Laurence A. Greenberg; Werner H. Stemer; Ralph E. Locher

(57) ABSTRACT

A leg pulling device has a traction device and a supporting device. At least one force or at least one pressure which is exerted on a patient by the supporting device upon the actuation of the traction device can be measured.

9 Claims, 3 Drawing Sheets

LEG PULLING DEVICE

BACKGROUND OF THE INVENTION

Field of the Invention

The invention relates to a leg pulling device having a traction device and a supporting device, wherein at least one force or at least one pressure which is exerted on a patient by the supporting device upon actuation of the traction device can be measured.

Brief Summary of the Invention

In multifarious uses within the context of hip endoprosthetic, hip arthroscopic and traumatological interventions, both exact leg positioning and leg fixing are of enormous importance. Independent adjustment of these two parameters permits the executing surgeon more rapid, more precise and as a result, not least, cost-efficient work on the hip joint of a patient. In addition, for the optimal positioning of the patient, for example during intra-operative x-ray monitoring without obstruction to vision, an extension of the lower extremities can be helpful or necessary. The functions described are offered only by few OP table systems found on the market. Although these afford the surgeon leg positioning, fixing and optional extension in the required degrees of freedom, he is provided with no information about the forces which occur in the process and possibly anatomically unacceptable positions of the lower extremities. As a result, it is possible for crushing, bruising and other damage to the patient to occur, which, as undesired side effects or even subsequent consequences of a surgical intervention, cause a not inconsiderable impairment to his quality of life.

The prior art discloses a leg pulling device in which a patient is positioned on an operating table, so that there is a supporting roller between his femurs, and the patient can be supported with his lower pelvic area against the supporting roller. One foot of the patient is fixed in an extension shoe. The extension shoe is rotatably mounted about a spindle axis on a threaded spindle, so that the extremity fixed in the extension shoe can also be rotated about the same axis and locked in the necessary angular position. A pulling force can be exerted on the leg of the patient by the threaded spindle. The pulling force can be generated by rotating a hand crank on the spindle. The pulling force is generated in the direction of the spindle axis, which means that a head of the thigh of the patient can be lifted out of his acetabular cup and a view of the affected points, such as joint cartilage, can be exposed.

The problem with the device from the prior art is that when the critical pulling forces are exceeded, crushing, bruising and other damage can be caused to the soft parts being supported by the supporting roller.

It is an object of the present invention to specify a leg pulling device with which such damage can be avoided.

The object is achieved by the leg pulling device as claimed. The dependent claims specify advantageous developments of the leg pulling device according to the invention.

According to the invention, a leg pulling device is specified which, firstly, has a traction device with which a pulling force can be exerted on a leg of a patient, and secondly a supporting device, which is arranged relative to the traction device such that the supporting device can support the patient counter to the pulling force exerted by the traction device. Irrespective of how the traction device and the supporting device are configured in practical terms, in this configuration the problem addressed by the invention occurs, that the patient can suffer damage as a result of the supporting process on the supporting device. The leg pulling device can optionally also be designated as a leg traction measuring device or be one such.

The pulling device can be arranged relative to the supporting device such that the force that can be generated by the traction device has a component which is aimed directly at the supporting device. In general, however, the force exerted by the traction device is itself not aimed directly at the supporting device but points past the latter, since in use the force exerted by the traction device is conducted to the supporting device via the body of the patient.

In one advantageous refinement, the leg pulling device can be arranged on an operating table. A lying surface of the operating table can, but does not have to be, viewed as part of the leg pulling device. The supporting device can advantageously be arranged on the lying surface of the operating table on which the patient lies during use.

The traction device can advantageously exert a force which has a component in the direction parallel to the lying surface of the operating table on which the patient lies during use. This component of the pulling force can advantageously be identical to the pulling force itself or represent the largest component of the pulling force. The force component lying in the direction parallel to the surface of the operating table is that which is critical for the execution of the operation.

According to the invention, the supporting device and/or the traction device has/have at least one sensor, with which at least one force or at least one pressure can be measured, which force or which pressure is exerted on the patient by the supporting device upon actuation of the traction device. It should be pointed out that the object according to the invention is achievable by both alternatives, both force sensors and pressure sensors. Advantageously, pressure sensors should be viewed here as special embodiments of force sensors, since they likewise measure forces but per unit area.

Sensors which measure only a force but not a pressure can be implemented simply and economically. On the other hand, pressure sensors permit more accurate measurements of the pressures actually acting on the patient. In many cases, a force sensor, with which a pressure is not directly measured, is sufficient however, since conclusions about the pressures which act on the patient can be drawn from measured forces. For example, a spectrum of anatomical shapes of the patient can be assumed and the pulling force can be limited such that it does not lead to damage to the patient under any of the anatomical conditions. Advantageously, a database can be provided which contains critical values for different groups of persons, such as children, adults, men, women, etc. Values can also be stored for different body conditions.

In an advantageous refinement of the invention, the supporting device can have the at least one pressure or force sensor. In a particularly advantageous refinement, the sensor can have or be a pressure measuring film, which is arranged on those surfaces of the supporting device which press on the body of the patient when a pulling force is exerted on the leg of the patient by means of the traction device. By using the pressure measuring film on the supporting device, the most accurate results can be achieved.

In an advantageous refinement of the invention, the supporting device can have at least two of the sensors, with which two mutually perpendicular force components in the direction parallel to the lying surface can be measured. In this refinement, a sensor therefore measures a force component acting on the supporting device in one direction and another sensor a force component acting on the supporting device in a direction perpendicular thereto.

Particularly advantageously, the supporting device can be supported on the lying surface by means of two mutually perpendicular guide carriages. To this end, for example, the supporting device itself can be supported on a first carriage, which permits a displacement of the supporting device in a first direction, and the supporting device, together with the first carriage, can be supported on a second carriage, which permits a movement of the supporting device and of the first carriage in a second direction perpendicular to the first direction. Advantageously, the first direction and the second direction can coincide with the mutually perpendicular directions in which forces can be measured with the two force sensors described above.

In an advantageous refinement of the invention, the supporting device can have or be a supporting roller, which is located with its roller axis at right angles on a lying surface on which the patient lies during the operation, for example the surface of the operating table. The roller can be arranged such that during proper use it is located between the femurs of the patient when the pulling force is exerted on the leg of the patient by the traction device. In this way, the roller supports the patient counter to said pulling force. The pressure measuring film described can optionally be arranged on the surface of said roller.

The traction device advantageously has a fixing device for fixing a foot of the patient when the pulling force is exerted on the leg as an extremity. The fixing device can, for example, be configured as an extension shoe. The traction device can then pull the fixing device in the direction of a longitudinal direction of the leg of the patient.

In an advantageous refinement, the fixing device can have an inclination sensor, with which the position of the fixing device about at least one axis, preferably about three axes, can be measured. In this way, the exact position of the affected leg in space can be detected.

The traction device can advantageously have a traction spindle, with which the pulling force on the extremity of the patient is adjustable. The traction spindle can, for example, be a threaded spindle, which is operable by a surgeon by means of a crank. The pulling force can thus be exerted in the direction of the spindle axis.

Advantageously, the leg pulling device according to the invention can have a microcontroller unit, with which measured values generated by the force or pressure sensors and optionally also by the inclination sensor can be evaluated, and with which, when critical threshold values of the forces measured by the force sensors, the pressures measured by the pressure sensor and/or the inclinations measured by the inclination sensor are exceeded, an alarm signal can be generated. Such threshold values can, for example, be provided ex works or determined experimentally in advance while taking into account the given operating conditions. In particular, they can be stored in the above-described database.

The invention is to be explained below by way of example by using figures. Identical designations identify identical or corresponding features. The features described in the examples can also be implemented independently of the practical example and combined among the various examples.

BRIEF DESCRIPTION OF THE SEVERAL VIEWS OF THE DRAWING

In the figures.

DESCRIPTION OF THE INVENTION

Figure 1:
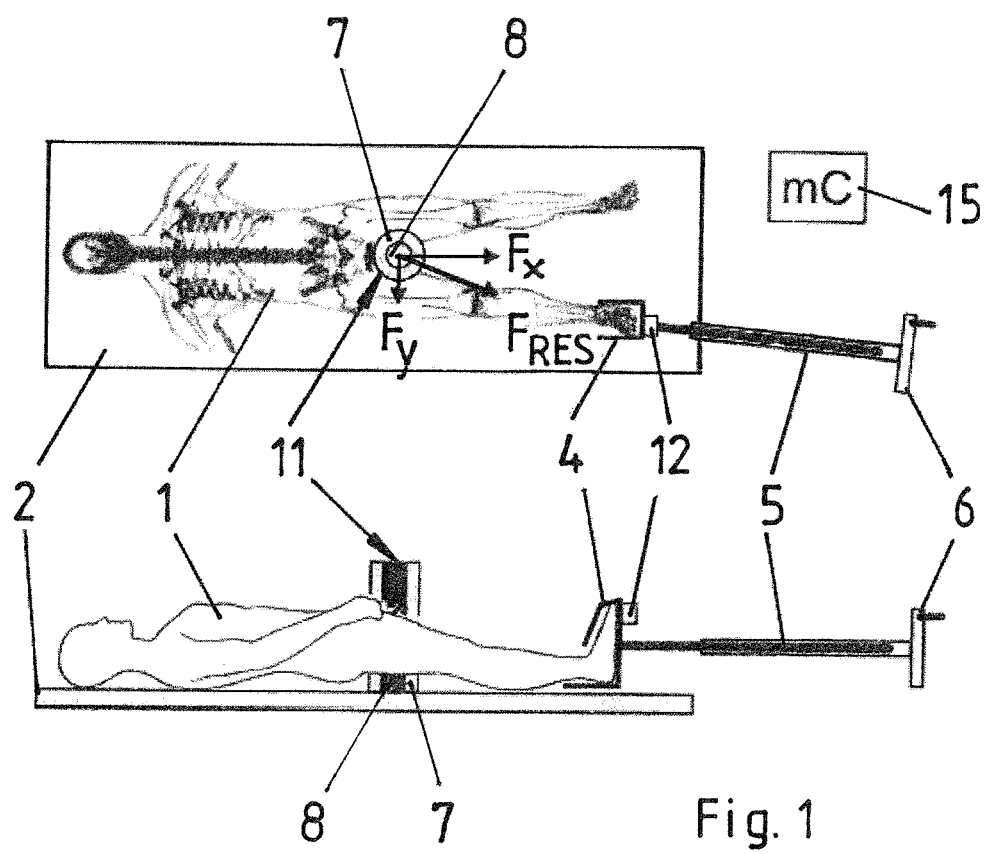
FIG. 1 shows an exemplary configuration of a leg pulling device according to the invention.

FIG. 1 shows a first exemplary configuration of a leg pulling device according to the invention in the application to a patient 1. The leg pulling device has a traction device 5, here a traction spindle, and a supporting device 11, here a supporting roller. The supporting roller of the supporting device 11 is arranged relative to the traction device 5 such that the supporting device 11 supports the patient 1 counter to the pulling force exerted by the traction device 5.

The patient 1 lies on a lying surface 2, here the surface of an operating table. The patient lies on his back and the supporting device is arranged between his thighs. The right-hand foot of the patient is fixed in an extension shoe 4 which is connected to the traction device 5. In this way, a pulling force can be exerted by the traction device 5 on the extension shoe 4 and therefore on the leg of the patient 1 in a longitudinal direction of the traction device 5.

In the example shown, the supporting device 11 has two force sensors 13, 14, with which force components $F_X$ and $F_y$ can be measured, so that a resultant force $F_{RES}$ can be calculated from the force components. Since the traction device 5 is configured here as a threaded spindle, the force exerted by the traction device 5 is adjustable by means of a crank 6, which is rotatable about the longitudinal axis of the traction device 5.

Arranged on the extension shoe 4 in the example shown is an inclination sensor 12, with which an inclination of the extension shoe 4 and therefore of the leg of the patient 1 about one, two or three axes can be determined. The device shown additionally has a microcontroller unit 15, with which the measurements from the force sensors 13, 14 and inclination sensors 12 can be evaluated.

With the configuration of the leg pulling device according to the invention shown in FIG. 1, the pulling force and the position of the affected extremity in space can be determined. The force vector $F_{RES}$ can be determined by means of the microcontroller unit 15. The microcontroller unit 15 measures the values and can give a surgeon a warning signal when critical threshold values are reached. In a corresponding way, the control unit 15 can also give a warning signal to the surgeon when a setting angle determined by means of the inclination sensor 12 results in a position of the extremity that is impermissible from an anatomical point of view.

Advantageously, a library in the form of a database can be stored in the microcontroller unit 15, containing information about the critical values for different groups of persons such as children, adults, men and women, and for different body conditions. The microcontroller unit 15 can additionally permit monitoring of a period of action of the pulling forces, which is likewise of great relevance for the surgical intervention.

Figure 2:
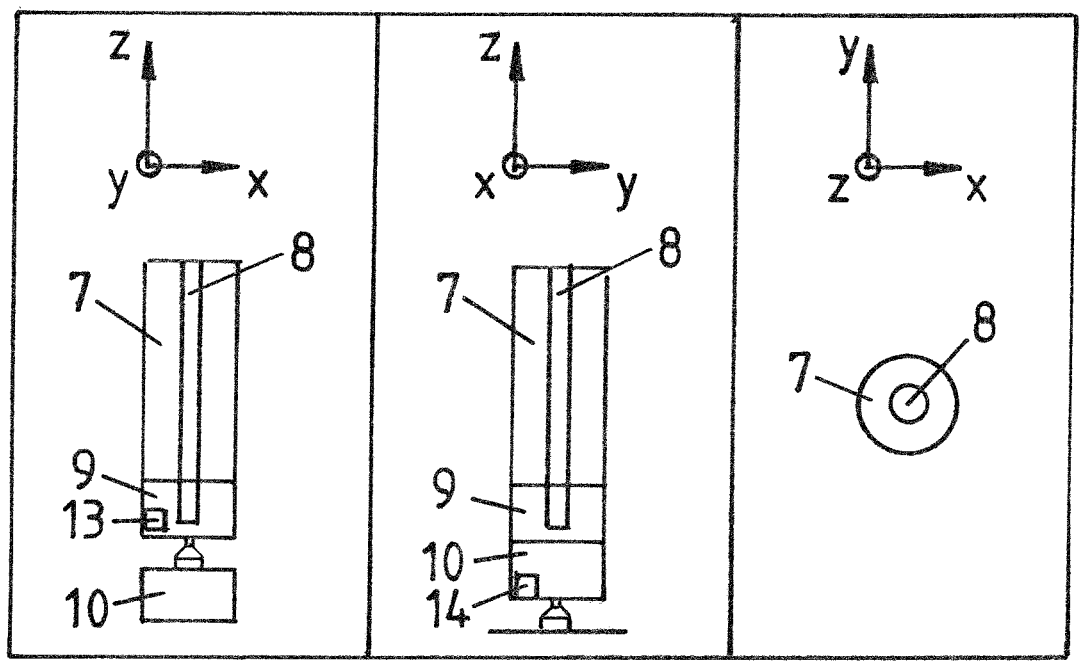
FIG. 2 shows an exemplary mounting of a supporting device.

FIG. 2 shows, by way of example, a supporting device 11 as can be used in the leg pulling device according to the invention. Here, the supporting device 11 is configured as a supporting roller and, in FIG. 2, is shown from three different perspectives, which are each indicated by the coordinate system marked.

The left-hand partial image here shows a section through the supporting device 11 in the xz plane in front view. The central partial image shows a section in the yz plane in side view, and the right-hand partial image shows a section in the xy plane in plan view.

The supporting roller of the supporting device 11 shown in FIG. 2 has a core rod 8, which is surrounded by a foam cushion 7. The foam cushion 7 therefore forms a cylinder, of which the cylinder axis coincides with the longitudinal axis of the rod 8. The supporting roller is supported on the lying surface 2 via two guide carriages 9 and 10. Here, the lower, second guide carriage 10 in the example shown is movable in the y direction, and the upper, first guide carriage 9 in the x direction. Together, the guide carriages 9 and 10 permit mobility of the supporting roller of the supporting device 11 in the xy plane.

Arranged in the first guide carriage 9 is a first force sensor 13, with which a force acting on the supporting roller of the supporting device 11 in the x direction can be measured. In addition, the second guide carriage 10 has a force sensor 14, with which a force in the y direction can be measured.

Figure 3:
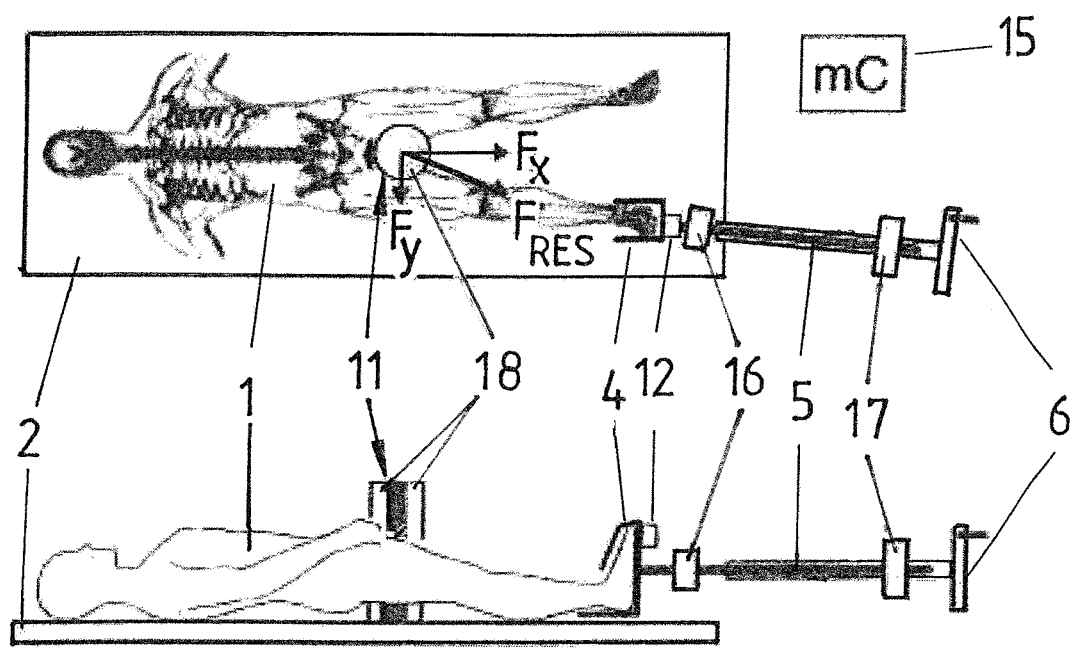
FIG. 3 shows a further exemplary configuration of a leg pulling device according to the invention.

FIG. 3 shows, by way of example, a further possible configuration of a leg pulling device according to the invention. Once more, a patient 1 lies on a lying surface 2, wherein the supporting device 11 is arranged between his thighs. The right-hand foot of the patient 1 is held by an extension shoe 4 which, as shown in FIG. 1, has an inclination sensor 12. On the extension shoe 4, by means of the traction device 5, a pulling force can be exerted on the leg of the patient 1 by rotating a crank 6. To this extent, the device shown in FIG. 3 corresponds to the device shown in FIG. 1.

In the example shown in FIG. 3, the supporting roller of the supporting device 11 has on its lateral cylindrical surface a pressure measuring film 18, with which a force exerted on the supporting roller by the patient 1 can be measured in a location-dependent manner. The pressure measuring film 18 can be provided in addition to or as an alternative to the force measurement shown in FIG. 2.

In the example shown in FIG. 3, the traction device 5 additionally has a pulling force sensor 16, with which the pulling force exerted on the extension shoe 4 by the traction device 5 can be measured directly. The pulling force sensor 16 can advantageously be provided on the supporting roller as an alternative to the force measurement shown in FIG. 2. The pulling force sensor 16 can additionally also be used in addition to or as an alternative to the pressure measuring film 18.

Furthermore, the traction device 5 shown in FIG. 3 has a torque sensor 17, with which a torque on the traction spindle of the traction device 5 can be detected and can be converted into the pulling force applied. In this way, too, conclusions can be drawn about the supporting force acting on the patient 1.

It should be pointed out that the form of the force measurement, the pressure measuring film 18, the pulling force sensor 16 and the torque sensor 17 shown in FIG. 2 represent advantageous alternatives. Although these sensors 16, 17, 18 can be combined with one another, according to the invention in principle one of these measuring devices is sufficient, however.

The invention claimed is:

1. A leg pulling device, comprising:
    a traction device for exerting a pulling force on a leg of a patient;
    a supporting device arranged relative to said traction device such that said supporting device supports a patient counter to a pulling force exerted by said traction device;
    said supporting device and/or said traction device having at least one sensor configured to measure a force or a pressure exerted on the patient by said supporting device upon an actuation of said traction device can be measured; and
    a lying surface, said supporting device having at least two of said sensors configured to measure two mutually perpendicular force components in a direction parallel to said lying surface; and
    two mutually perpendicular guide carriages supporting said supporting device on the lying surface, said two mutually perpendicular guide carriages being oriented in mutually perpendicular direction in which the force components can be measured by the force sensors.

2. The leg pulling device according to claim 1, wherein said at least one sensor is mounted to said supporting device.

3. The leg pulling device according to claim 1, wherein said at least one sensor has or is a pressure measuring film arranged on a surface of said supporting device pressing on the patient upon the actuation of said traction device.

4. The leg pulling device according to claim 1, comprising a lying surface for supporting the patient, and wherein said supporting device has a supporting roller, which is upright on said lying surface and arranged to be located between the patient's femurs when a pulling force is exerted on a leg of the patient by said traction device, and wherein said supporting device supports the patient counter to the pulling force.

5. The leg pulling device according to claim 1, wherein said traction device comprises a fixing device for fixing a foot of the patient and an inclination sensor mounted to said fixing device and configured to measure a position of said fixing device about at least one axis.

6. The leg pulling device according to claim 5, wherein said inclination sensor is configured to measure a position about three axes.

7. The leg pulling device according to claim 1, wherein said traction device includes a traction spindle configured to adjust a pulling force on the leg of the patient.

8. The leg pulling device according to claim 1, further comprising a microcontroller unit configured to evaluate measurements generated by said at least one sensor, and to generate an alarm signal when critical threshold values for the force or pressure measured by said at least one sensor are exceeded.

9. The leg pulling device according to claim 8, wherein said micro-controller unit is further configured to evaluate measurements generated by a plurality of force sensors and pressure sensors, and an inclination sensor.

* * * * *